(12) United States Patent
Saur et al.

(10) Patent No.: US 9,933,606 B2
(45) Date of Patent: Apr. 3, 2018

(54) SURGICAL MICROSCOPE

(71) Applicant: Carl Zeiss Meditec AG, Jena (DE)

(72) Inventors: Stefan Saur, Aalen (DE); Marco Wilzbach, Stuttgart (DE); Christian Wojek, Aalen (DE); Frank Rudolph, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 22 days.

(21) Appl. No.: 14/721,270

(22) Filed: May 26, 2015

(65) Prior Publication Data

US 2015/0342697 A1    Dec. 3, 2015

(30) Foreign Application Priority Data

May 27, 2014  (DE) .................. 10 2014 007 909

(51) Int. Cl.
*G02B 21/00*   (2006.01)
*A61B 19/00*   (2006.01)
(Continued)

(52) U.S. Cl.
CPC .......... *G02B 21/0012* (2013.01); *A61B 90/20* (2016.02); *A61B 90/90* (2016.02);
(Continued)

(58) Field of Classification Search
CPC .... G02B 21/00; G02B 21/0012; G02B 21/06; G02B 21/22; G02B 21/24; G02B 21/36; G02B 21/361; G02B 21/364; G02B 21/367; G02B 21/248; A61B 5/00; A61B 5/0059; A61B 5/06; A61B 3/14; A61B 3/102; A61B 19/10; A61B 19/5223; A61B 19/5244;
(Continued)

(56) References Cited

U.S. PATENT DOCUMENTS 5,790,307 A    8/1998  Mick et al.
7,477,764 B2 *  1/2009  Haisch ............... A61B 34/20
                                                    128/922

(Continued)

FOREIGN PATENT DOCUMENTS

CN    101170961 A    4/2008
DE    102 52 837 A1  6/2004
(Continued)

OTHER PUBLICATIONS

English tranlation of DE102007054450 A1, machine translated on Aug. 31, 2016.*

(Continued)

*Primary Examiner* — Jie Lei
(74) *Attorney, Agent, or Firm* — Patent Portfolio Builders PLLC

(57) ABSTRACT

A surgical microscope comprises microscopy optics, a camera, a display system and a controller comprising a data memory storing object data of at least one surgical tool. The microscopy optics are variable optics for changing an imaging scale of an imaging of a field of view onto the camera. The controller is configured to process the camera images and to identify the at least one tool in the camera images by object recognition using the object data of the at least one tool and the set imaging scale.

12 Claims, 3 Drawing Sheets

(51) Int. Cl.
*A61B 90/90* (2016.01)
*A61B 90/20* (2016.01)
*A61B 90/00* (2016.01)
*A61B 34/20* (2016.01)

(52) U.S. Cl.
CPC ............... *A61B 2034/2065* (2016.02); *A61B 2090/3735* (2016.02)

(58) Field of Classification Search
CPC . A61B 90/20; A61B 90/90; A61B 2034/2065; A61B 2090/3735; G06T 7/0012
USPC ............... 359/381, 363, 368, 369, 376, 378; 351/206; 600/476, 429, 424, 426; 382/128, 130, 131
See application file for complete search history.

(56) References Cited

U.S. PATENT DOCUMENTS

| | | | |
|---|---|---|---|
| 2004/0167742 | A1 | 8/2004 | Haisch |
| 2005/0024586 | A1 | 2/2005 | Teiwes et al. |
| 2006/0293557 | A1 | 12/2006 | Chuanggui et al. |
| 2007/0265495 | A1 | 11/2007 | Vayser |
| 2009/0244485 | A1 | 10/2009 | Walsh et al. |
| 2011/0015518 | A1 | 1/2011 | Schmidt et al. |
| 2011/0046637 | A1 | 2/2011 | Patel et al. |
| 2012/0182409 | A1 | 7/2012 | Moriyama et al. |
| 2012/0219185 | A1 | 8/2012 | Hu et al. |
| 2012/0226150 | A1 | 9/2012 | Balicki et al. |
| 2012/0253200 | A1 | 10/2012 | Stolka et al. |
| 2012/0259204 | A1 | 10/2012 | Carrat et al. |
| 2012/0290134 | A1 | 11/2012 | Zhao et al. |
| 2013/0016185 | A1 | 1/2013 | Stolka et al. |
| 2013/0201449 | A1* | 8/2013 | Walsh ............... A61B 3/102 351/206 |
| 2013/0218024 | A1 | 8/2013 | Boctor et al. |
| 2014/0024949 | A1 | 1/2014 | Wei et al. |

FOREIGN PATENT DOCUMENTS

| | | | | |
|---|---|---|---|---|
| DE | 10 2007 054 450 | A1 | 5/2008 | |
| WO | 2006/095027 | A1 | 9/2006 | |
| WO | 2009/120544 | A1 | 10/2009 | |
| WO | 2012/130449 | A1 | 10/2012 | |
| WO | WO 2012/130449 | * | 10/2012 | ............... A61B 5/00 |

OTHER PUBLICATIONS

Extended European Search Report issued in corresponding European application No. 15 001 595.6 dated Oct. 26, 2015.
Hinterstoisser, S. et al., "Multimodal Templates for Real-Time Detection of Texture-less Objects in Heavily Cluttered Scenes," 2011 IEEE International Conference on Computer Vision (ICCV), Nov. 6-13, 2011, Barcelona, Spain, pp. 858-865, ISSN: 1550-5499; Print ISBN: 978-1-4577-1101-5.
Dollár, P. et al., "The Fastest Pedestrian Detector in the West," British Machine Vision Conference (BMVC), Sep. 2010, pp. 68.1-68.11, BMVA Press, doi: 10.5244/C.24.68.
Benenson, R. et al., "Pedestrian detection at 100 frames per second," 2012 IEEE Conference on Computer Vision and Pattern Recognition (CVPR), Jun. 16-21, 2012, Providence, Rhode Island, USA, pp. 2903-2910, ISSN: 1063-6919, Print ISBN: 978-1-4673-1226-4.
Dalal, N. et al., "Histograms of Oriented Gradients for Human Detection," 2005 IEEE Computer Society Conference on Computer Vision and Pattern Recognition (CVPR), Jun. 25, 2005, San Diego, California, USA, pp. 886-893, vol. 1, ISSN: 1063-6919, Print ISBN: 0-7695-2372-2.
Viola, P. et al., "Rapid Object Detection using a Boosted Cascade of Simple Features," Proceedings of the 2001 IEEE Computer Society on Computer Vision and Pattern Recognition (CVPR), 2001, pp. I-511-I-518, vol. 1, ISSN: 1063-6919; Print ISBN: 0-7695-1272-0.
Leibe, B. et al., "Robust Object Detection with Interleaved Categorization and Segmentation," International Journal of Computer Vision, Special Issue on Learning for Vision and Vision for Learning, vol. 77, No. 1-3, May 2008, pp. 1-26.
Mikolajczyk, K. et al., "Scale & Affine Invariant Interest Point Detectors", International Journal of Computer Vision, vol. 60, No. 1, 2004, pp. 63-86, Kluwer Academic Publishers, Manufactured in The Netherlands.
German Office Action, with translation thereof, for corresponding DE application No. 10 2014 007 909.0 dated Jan. 13, 2015.
Office Action in corresponding European Application No. 15 001 595.6 dated Feb. 16, 2017. (References D1 through D7 were previously made of record in Information Disclosure Statements submitted on Oct. 7, 2015 and Nov. 12, 2015).
Office Action in corresponding European Application No. 15 001 595.6 dated May 29, 2017. (Reference US2004/167742A1 was previously made of record in an Information Disclosure Statement submitted on Oct. 7, 2015).

* cited by examiner

SURGICAL MICROSCOPE

CROSS-REFERENCES TO RELATED APPLICATIONS

The present application claims priority of Patent Application No. 10 2014 007 909.0, filed May 27, 2014 in Germany, the entire contents of which are incorporated by reference herein.

FIELD

The present invention relates to surgical microscopes assisting the usage of surgical tools during microsurgical interventions.

BACKGROUND

During such interventions, a surgeon observes the field of operation using a microscope and performs manipulations using a surgical tool. In comparison to surgical interventions performed whilst observing with the naked eye, microsurgical interventions during which the surgeon perceives the tissue to be manipulated and the tool used therefore as a microscopic image are difficult to perform. It is desirable to equip the microscope so that work is simplified for the surgeon and, for example, so that data is displayed in the microscopic image or measurements are performed automatically. Possible measures for assisting depend on the progress of the intervention as different assistive measures are desirable or possible in different stages of the intervention. In particular, different surgical tools are used in different stages of the intervention. Therefore, desire raised to automatically recognize tools handled by the surgeon and contained in the object field of the microscope and to perform specific measures in dependence of the recognized tool.

Such automated recognition of tools in microscopic images requires automated image processing performing object recognition. During the object recognition, structures contained in the image are compared to a series of prospects and a corresponding prospect is recognized when a sufficient correlation is achieved.

It has been shown that a sufficiently faultless identification of tools in question in microscopic images is not possible at a sufficient certainty and in real-time using conventional methods of object recognition.

SUMMARY

Therefore, it is an object of the present invention to suggest a surgical microscope providing automated recognition of surgical tools in real-time.

According to embodiments, a surgical microscope is suggested which comprises: microscopy optics, a camera, a display system and a controller, wherein the microscopy optics are configured to image a field of view onto the camera, wherein the camera is configured to obtain two-dimensional camera images of the field of view and to generate image data representing the camera images, wherein the microscopy optics are variable optics configured to change an imaging scale of the imaging of the field of view onto the camera, wherein the controller comprises a data memory storing object data of at least one surgical tool, wherein the controller is configured to receive the image data from the camera and to process the camera images represented by the image data and to identify the at least one surgical tool in the camera images by object recognition using the object data of the at least one surgical tool and the set imaging scale.

The inventors found that the identifying of tools in the camera images of a conventional surgical microscope is problematic and attributed this to the fact that a surgeon occasionally changes the magnification provided by the microscopy optics and/or changes the distance from the object region to the microscopy optics. These changes are not predictable for an automated controller and are performed to an extent yielding unsatisfactory results when applying conventional techniques of object recognition on the camera images. Therefore, as a solution, it is suggested to take the set imaging scale of the microscopy optics into account during the object recognition. If this imaging scale is not taken into account, object data of a plurality of models of the at least one tool must be stored in the data memory. Accordingly, a multiple times enlarged amount of object data must be taken into account during the object recognition which may lead to a slower, imprecise and unreproducible object recognition. In comparison to that, by taking the imaging scale of the imaging during the object recognition into account, the computing time necessary for the object recognition can be reduced considerably. Therefore, the object recognition can be performed faster and more reliable at the same time. Object recognition and identifying an object may imply that the object, e.g. a surgical tool, present in the camera images may be identified among a set of predetermined objects, e.g. among a set of predetermined surgical tools. Therefore, by object recognition, the controller may determine which one of at least one predetermined tool is present in the camera images.

The data memory stores the object data of the at least one surgical tool. In particular, the object data of the tools, which are to be used during a planned surgical intervention, are stored in the data memory. The object data comprise geometry data representing the geometry of the respective surgical tool. For example, the geometry data represent the physical extent, such as length and width, and an orientation of surfaces of the tool at different locations of the tool. The geometry data may be CAD-data, for example, generated during the process of construction of the tool using a computer-aided-design-tool (CAD-tool). Furthermore, the object data may comprise additional data characterizing the tool and its visual appearance in the camera images. For example, these data represent a surface configuration, such as a surface texture, an edge distribution or the same. The object data as well as the geometry data may be stored in the data memory prior to the intervention, and in particular prior to the obtaining of camera images by the camera.

According to exemplary embodiments, the object recognition works according to a template-matching-technique, a sliding-window-technique and/or a Hough-voting-technique.

According to exemplary embodiments, the identifying of the at least one surgical tool comprises generating data representing at least one of an identifier used for the tool, a position of the tool in the field of view and an orientation of the tool in the field of view. The identifier may identify a tool so that the tool may be distinguished from other predetermined tools. That is, the identifier may be used to identify a tool from a group of predetermined tools. The identifier may be a numeric code, a symbol or the like.

Different predetermined measures may be triggered in dependence of the identified tool.

According to further exemplary embodiments, the identified tool is compared to a predetermined tool to be used at a specific state of the intervention. Therefore, it can be determined whether the surgeon unintentionally uses a wrong tool currently not intended for use and it is possible to subsequently issue a corresponding warning.

According to an exemplary embodiment, the predetermined measure corresponds to performing an OCT measurement in a region of the field of view of the microscopy optics containing a distal end of the identified tool. For this, it is necessary to determine the tool in use and its position and orientation in the field of view by the object recognition in order to be able to subsequently direct the OCT measurement beam to the corresponding locations in the field of view.

According to exemplary embodiments, a movement pattern of the identified tool is recognized in the field of view and a specific measure is performed if the predetermined movement pattern is identified. Therefore, in this manner, the surgeon may control properties and functionalities of the microscope, for example by means of gestures.

The display system of the surgical microscope may comprise a display for displaying an image generated from the data representing the camera images. The displayed image may substantially correspond to the camera image obtained by the camera. However, it may also be modified with respect to the camera image in that specific areas are highlighted by color or brightness, for example. The displayed image may also represent information such as letters, numbers or other symbols.

According to exemplary embodiments, the display system comprises an ocular of the microscopy optics, wherein the microscopy optics are configured to project the image displayed by the display into a beam path of the ocular.

According to exemplary embodiments, the microscopy optics comprise at least one sensor configured to detect the set imaging scale and to transmit data representing the detected imaging scale to the controller, wherein the controller is configured to obtain the set imaging scale of the imaging from these data.

According to further exemplary embodiments, the controller comprises a user interface configured to receive data representing a magnification of the imaging desired by a user, wherein the microscopy optics comprise an actuator for changing the imaging scale, wherein the actuator is controlled by the controller, and wherein the controller is configured to control the actuator in dependence of the data representing the desired magnification. Herein, the controller may determine the imaging scale from the data representing the desired imaging scale or the desired magnification.

The imaging scale of the imaging by the microscopy optics may be changed by changing a setting of a zoom system of the microscopy optics. Furthermore, the imaging scale may be changed by disposing the microscope closer to the object region or further away from it. For this, the microscopy optics may comprise an objective lens having components being displaceable relative to each other in order to change a working distance. The working distance and the setting of the zoom system together determine the imaging scale of the microscopy optics. The controller may determine an expected size of the surgical tool in the camera images based on the determined set imaging scale and may use this expected size for the object recognition.

Further embodiments are directed to a method of operating a surgical microscope.

According to an exemplary embodiment, a method of operating a surgical microscope, in particular a surgical microscope according to the embodiments described herein, comprises: storing object data of at least one surgical tool in a data memory; imaging a field of view onto a camera; obtaining two-dimensional camera images of the field of view using the camera while an imaging scale of optics providing the imaging is set according to a value; generating image data representing the camera images; processing the camera images; and identifying the at least one surgical tool in the camera images by object recognition using the object data of the at least one surgical tool and the value of imaging scale.

According to further exemplary embodiments, the method further comprises triggering a measure in dependence of the identified at least one surgical tool. Herein, the method may further comprise at least one of performing a measurement, in particular an OCT measurement, and changing an information displayed by a display system.

According to further exemplary embodiments, the method further comprises determining the value of the imaging scale. For example, the value may be determined by measuring a measurement value representing the value of the imaging scale. Alternatively or in addition, the value may be determined based on a magnification of the imaging provided by the optics.

According to further exemplary embodiments, the method further comprises determining an expected size of the at least one surgical tool in the camera images based on the object data of the at least one surgical tool and the value of the imaging scale, and using the expected size of the at least one surgical tool for the object recognition.

According to further exemplary embodiments, the object recognition uses a technique selected from a group of techniques, wherein the group of techniques comprises a template matching technique, a sliding window technique and a Hough voting technique.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
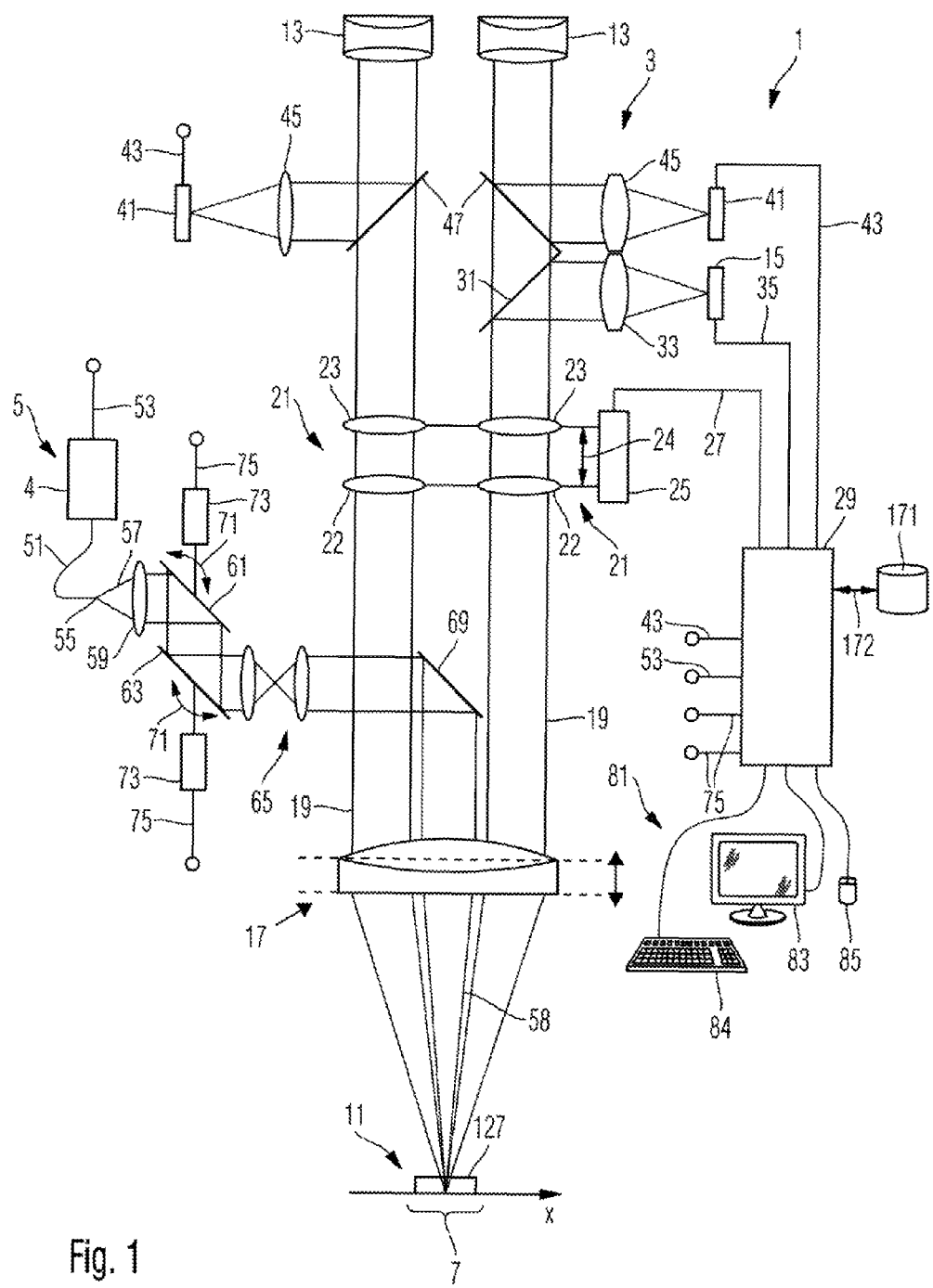
FIG. 1 shows a schematic illustration of an embodiment of a surgical microscope.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 is a schematic illustration of a surgical microscope 1. The surgical microscope 1 comprises imaging optics 3 configured to generate images of a field of view 7 located within an object region 11. The imaging of the field of view 7 using the imaging optics 3 of the illustrated exemplary embodiment is performed via a pair of oculars 13 into which a surgeon may view with both his eyes. Furthermore, the field of view 7 is imaged onto a camera 15 obtaining images of the field of view 7 and generating data representing the images.

For this, the optics 3 comprise an objective lens 17 which may comprise one or multiple lens elements and which, in accordance with the illustrated example, may image the field of view to infinity. In the beam path behind the objective lens 17, each of two beam bundles 19 is guided through a zoom lens assembly 21 capable of changing an imaging scale of the optics. For this, the two zoom lens assemblies 21 each comprise at least two groups of lenses 22 and 23 displaceable relative to each other in beam direction of the beam bundles 19 as indicated by an arrow 24 in FIG. 1. The displacement of the two groups of lenses 22 and 23 relative to each other is controlled by an actuator 25 which in turn is controlled by a controller 29 via a control wire 27 for setting the imaging scale of the optics 3.

Behind the zoom lens assembly 21, the beam bundles 19 enter the oculars 13. However, a portion of the light of the right one of the beam bundles 19 illustrated in FIG. 1 is redirected by a partially transparent mirror 31 and is directed onto the camera 15 by camera adapter optics 33 so that the camera can detect an image of the field of view 7 of the object region 11. The data generated by the camera 15 are transmitted to the controller 29 via a data wire 35.

The optics 3 further comprise two electronic image displays 41 fed with image data by the controller 29 via a data wire 43. The images displayed by the image displays 41 are each projected into the beam path towards the oculars 13 by projecting optics 45 and a partially transparent mirror 47 disposed in the beam bundles 19 so that a user viewing into the oculars 13 may perceive the images displayed by the displays 41 in superposition with the image of the field of view 7 of the object region 11.

The surgical microscope 1 further comprises an OCT system 5 for performing OCT measurements. The OCT system 5 comprises an OCT device 4 having an appropriate light source of short coherence and an interferometer, both not illustrated in FIG. 1, wherein OCT measurement light is emitted from the OCT device 4 via a light guiding fiber 51 so that the measurement light may be incident onto an object to be measured and measurement light returning from the object may re-enter the fiber so that the OCT device 4 may examine this returning measurement light and output data representing the measurement. In particular, the OCT device 4 may perform a depth scan also referred to as A-scan, the data of which represent intensities of backscattered measurement light in dependence of the depth. The OCT device 4 is controlled by the controller 29 via a control and data wire 53. The controller 29 also receives the measurement data generated by the OCT system 5 via this wire 53.

The OCT system 5 further comprises collimation optics 59 collimating OCT measurement light 57 emitted from an end 55 of the fiber 51 into a measurement light beam 58. The measurement light beam 58 is deflected at two deflecting mirrors 61 and 63, propagates through projecting optics 65, is incident onto a mirror 69 and is directed by the mirror 69 through the objective lens 17 onto the object region 11. An object 127 may be disposed in the object region 11 which backscatters OCT measurement light so that the measurement light backscattered by the object 127 propagates along the reverse path through the objective lens 17, the projecting optics 65 and the collimating optics 59 so that at least a portion of this light is coupled into the fiber 51 and arrives at the OCT device 4 where it is examined using the interferometer.

The mirrors 61 and 63 are tiltably disposed in order to deflect the OCT measurement light beam so that the OCT measurement light beam may be incident onto selectable locations within the field of view 7 by setting tilt settings of the mirrors 61 and 63. The tiltability of the mirrors 61 and 63 is indicated by arrows 71 in FIG. 1. The tilt setting of the mirrors 61 and 63 is set by actuators 73 controlled by the controller 29 via control wires 75. Therefore, by driving the actuators 73, the controller 29 may select the location of the object region 11 onto which the OCT measurement light beam is incident.

The controller 29 further comprises a user interface comprising a monitor 83 as an illustrating medium, and a keyboard 84 and a mouse 85 as input media. The user interface also comprises the displays 41 for coupling images generated by the controller 29 into the beam paths to the oculars 13.

In the exemplary embodiment described herein, the surgical microscope is used to assist a microsurgical intervention on a tissue using a surgical tool.

Figure 2:
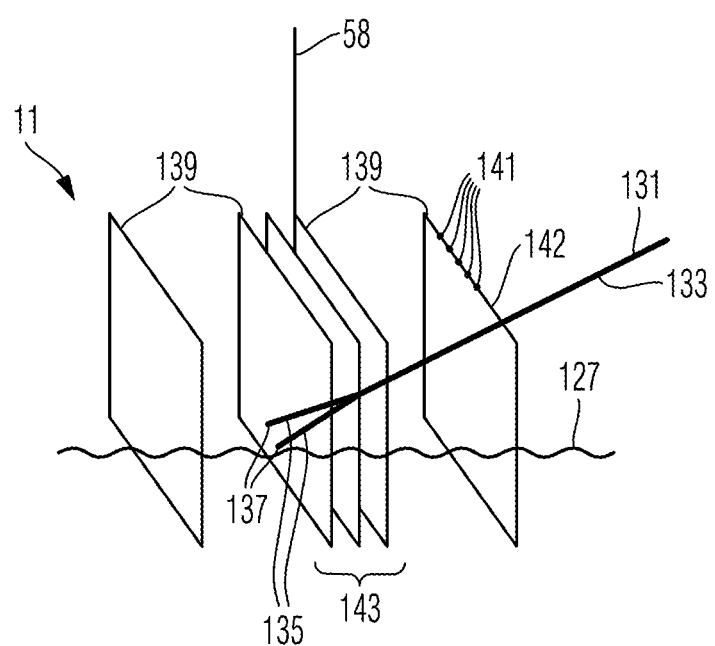
FIG. 2 shows a schematic illustration of an object region of the surgical microscope of FIG. 1.

FIG. 2 schematically shows such a situation. Therein, the surgical tool has the numeral 131 and has a shaft 133 at the front end of which a pair of tweezer-like grippers 135 are located, each having a distal end 137. The tool 131 may be used to manipulate the tissue 127, such as the retina of an eye, which may be very sensitive. Therefore, unintentional touches of the tissue 127 and an application of pressure to this tissue should be avoided. The surgical microscope 1 provides a possibility of visual supervision when approaching the tissue 127 with the tool 131.

The process of approaching the tool 131 to the tissue 127 within the field of view 7 may be visually observed by the surgeon in that the surgeon views into the oculars 13 and observes the image of the field of view 7. It is also possible that the surgeon or his assistant observe the image of the field of view 7 on the monitor 83 when the controller 29 displays the image of the field of view 7 detected by the camera 15 thereon. In addition, said image may also be displayed using head mounted display devices.

However, it is difficult to estimate the distance between the tool 131 and the surface of the tissue 127, in particular, the distance from the distal ends 137 to the surface of the tissue 127 by observing the images of the field of view 7 obtained by the optics 3 as the image represents a top view onto the surface of the tissue 127 while the tool 131 is disposed before the retina.

Therefore, in the illustrated example, the controller 29 triggers the OCT system 5 to perform measurements along sections containing portions of the tool 131 and portions of the retina 127. In particular, the controller may trigger the OCT system to perform one or multiple B-scans. FIG. 2 shows some exemplary areas 139 in which B-scans are performed. For performing a B-scan, the OCT measurement light beam 58 is directed to a plurality of locations 141 one after another, wherein the locations are disposed along a straight line 142. At each of the locations 141, a depth scan (A-scan) is performed. The data representing the depth scans are transmitted from the OCT system 5 to the controller 29.

The position and the orientation of the areas 139, in which the B-scans are performed, are determined by the controller by analyzing the images of the field of view 7 obtained by the camera 15. For this, the controller 29 performs object recognition in order to identify the tool 131 in the camera images and to determine the position and the orientation of the tool 131 relative to the object region 11 and the field of view 7. Then, the locations 141, where depth scans are performed, are determined and, in particular, determined so that depth scans are performed at locations 141 where the tool 131 is located in the field of view as well as at locations 141 where the tool 131 is not located in the field of view. Therefore, some of the performed depth scans contain the tool and other depth scans do not contain the tool. Herein, the depth scans may be performed at a higher spatial density and/or at a higher rate in the region where the distal ends 137 of the tool 131 are located. This is indicated in FIG. 2 in that the distances between adjacent areas 139 of the B-scans are small in a region 143 of the distal ends 137 compared to regions at greater distances from the distal end 137.

The B-scans may be displayed by display system of the microscope and the surgeon may estimate the distance between the tool and the surface of the tissue 127 more simply by observing the images of the B-scans performed at the distal end of the tool. This requires that the surgical tool 131 is recognized correctly and quickly in the camera images. The object recognition used for this accounts for the imaging scale used by the microscopy optics for the imaging of the field of view onto the camera. This imaging scale may be known to the controller 29 as the controller controls the set magnification of the zoom system 21 via the actuator 25. However, it is also possible that a sensor is provided at the zoom systems 21 and measures the relative position of the lenses 22 and 23 relative to each other so that the controller may determine the imaging scale from a signal of this sensor. The imaging scale desired by a user may be changed by, for example, operating a knob of the microscope which mechanically changes the distance between the lenses 22 and 23 or the user interface of the controller 29 may comprise a setting element operated by the mouse 85, for example, in order to change the imaging scale.

The object recognition can be performed quickly and reliably using the imaging scale provided by the microscopy optics.

Figure 3:
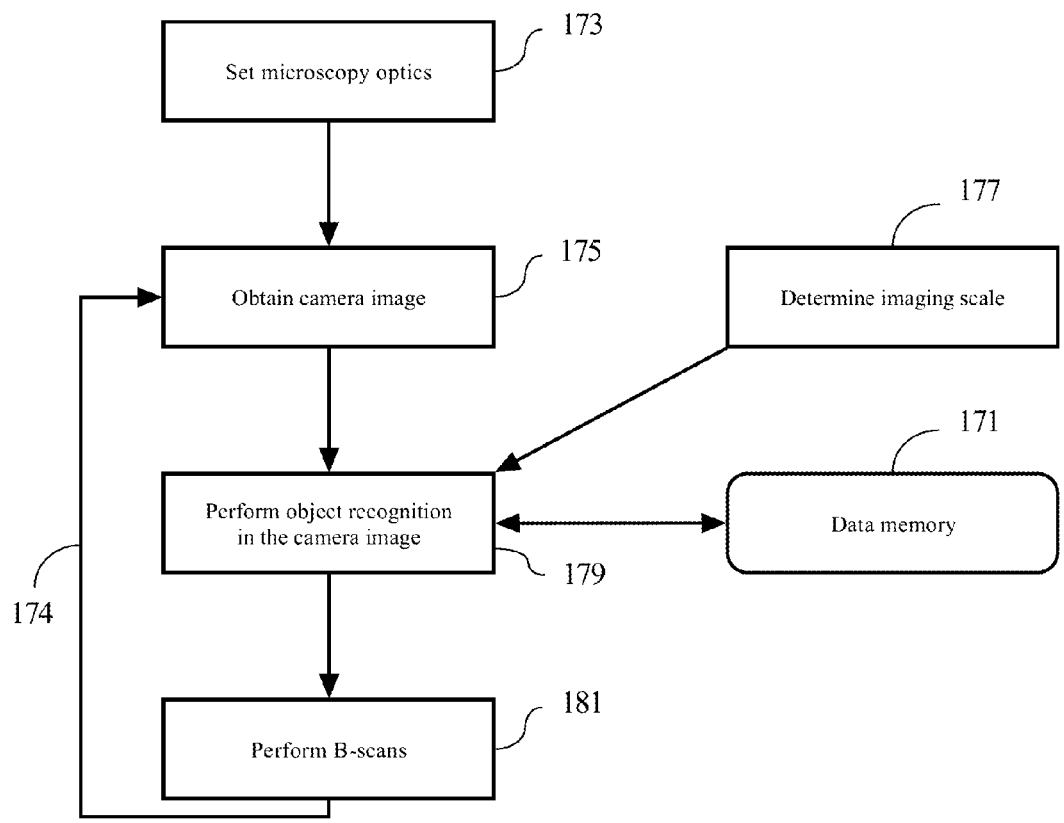
FIG. 3 shows a flowchart illustrating a workflow of the surgical microscope of FIG. 1.

A workflow of the surgical microscope of FIG. 1 is described in more detail with reference to the flowchart illustrated in FIG. 3.

Prior to the surgical intervention, object data of the surgical tools to be used during the intervention are stored in a data memory 171. The data memory 171 is connected to the controller 29 via a data wire 172 (see FIG. 1).

The approaching of the tool to the tissue is tracked by the surgical microscope. For this, the microscopy optics 3 of the surgical microscope are positioned relative to the tissue of the eye so that the region of the tissue to be manipulated is disposed in the field of view 7 and the magnification provided by the microscopy optics is set in step 173. Then, in step 175, a camera image is obtained. The obtained camera image is analyzed subsequently. The step 175 of obtaining the image and the subsequent analysis are repeated in a loop 174 and performed, for example, 15 times per second until the intervention is finished. The analysis of the camera image comprises an object recognition in the camera image in step 179 and, in particular, using the object data of the tools stored in the data memory 171. The object recognition is performed also taking the imaging scale into account provided by the microscopy optics for the imaging of the field of view onto the camera. This imaging scale is determined in step 177.

Typical values of ranges for the magnification are limited to values between a 1.0-fold and a 15-fold magnification. Therefore, also the size of the surgical tools in the camera images may vary strongly. A tool having a width of only 10 pixels at a magnification of the imaging of 1.0 has a width of roughly 150 pixels at a largest magnification of 15. These changes of the magnification impede conventional object recognition. However, in the described present embodiment, the magnification of the imaging is taken into account.

The object recognition may be performed according to different principles. According to an example, the object recognition is performed according to the template-matching-technique. Herein, during a training period, an expectable scale range is considered by discretizing the scale range. For example, the scale range may be discretized into 15 size steps. For each discrete size, one or multiple representative templates of the surgical tool are generated from its CAD-data. Then, during object recognition, all generated templates are slided in x- and y-direction across the image to be analyzed in order to examine whether a template correlates and matches to the current image content. In this case, the surgical tool is recognized at the corresponding position as a template having a size learned during the training period. As the magnification of the imaging and the previously performed discretizing of the scale range into the assumed 15 size steps is considered, it is not necessary to examine all templates of all 15 size steps. Instead, it may be sufficient to examine those templates having a size step which corresponds to the size step closest to the set magnification or having the two size steps adjacent to that. This considerably reduces the computing time necessary for the object recognition.

According to another example, the object recognition is performed according to the sliding-window-technique. Herein, the scale range is considered first during the object recognition as the objects are normalized to a unit size during the training period. The unit size may correspond to a magnification of the imaging of 1.0, for example. The unit models of the surgical tools thus obtained are scaled during the object recognition with a factor corresponding to the magnification of the imaging. The unit models scaled accordingly are slided across the image until an increased correlation is found. Similar to the previously described template-matching-technique, a significant reduction of the computing time may be achieved by taking the magnification into account.

According to another example, the object recognition is performed according to a voting-technique. During this technique, in a detection step, individual recognized features are accumulated to object hypothesis in a voting method such as the Hough voting. Individual features are found by so-called key point detectors and their local environment is described by means of descriptors (e. g. SIFT). Also for this method, the training data are normalized to a unit size. Therefore, it is known how large the expectable local features should be for a specific object size and magnification, respectively. Therefore, on the one hand, a search range of the key point detectors may be limited appropriately and, on the other hand, only those ranges must be considered during the accumulating of votes in Hough-space which are consistent with the magnification. Therefore, the object recognition may be accelerated as the search space may be reduced by taking the magnification of the imaging into account.

In step 181, after the object recognition in the camera image in step 179, B-scans are performed as described with reference to FIG. 2.

Performing the B-scans in step 181 is just an example of a measure performed in dependence of the tool identified in the camera images. In general, arbitrary dependent measures may be performed. Further exemplary measures comprise controlling a function of the microscope in dependence of a gesture made with the tool within the object region. Further, the recognized tool may be compared to a predetermined tool which is to be used during a specific state of the surgical intervention. If the identified tool does not correspond to this tool, a warning signal such as a warning sound may be output by the controller.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A surgical microscope comprising:
microscopy optics;
a camera;
a display system; and
a controller;
wherein the microscopy optics are configured to image a field of view onto the camera;
wherein the camera is configured to obtain two-dimensional camera images of the field of view and to generate image data representing the camera images;
wherein the microscopy optics are variable optics configured to change an imaging scale of the imaging of the field of view onto the camera;
wherein the controller comprises a data memory storing object data of each member of a group of plural different surgical tools;
wherein the controller is configured to:
receive the image data from the camera and to process the camera images represented by the image data;
determine an expected size of a surgical tool in the camera images based on the object data of the members of the group of plural different surgical tools and the imaging scale; and
use the determined expected size of the surgical tool to identify the surgical tool in the camera images by object recognition, the object recognition including:
limiting a search space of the object recognition by using the determined expected size of the surgical tool in the camera images;
using the object data of the members of the group of plural different surgical tools and the imaging scale; and
within the limited search space, selecting, from the members of the group of plural different surgical tools, a member corresponding to the surgical tool in the camera images.

2. The surgical microscope according to claim 1, wherein the identifying of the surgical tool in the camera images by object recognition comprises generating data representing at least one of: an identifier used for the surgical tool, a position of the surgical tool in the field of view, and an orientation of the surgical tool in the field of view.

3. The surgical microscope according to claim 1, wherein the controller triggers a measure based on the surgical tool.

4. The surgical microscope according to claim 3, wherein the measure comprises one of: performing an OCT measurement, and changing an information displayed by the display system.

5. The surgical microscope according to claim 1, wherein the display system comprises a display for displaying an image, wherein the controller generates data representing the displayed image based on the camera image.

6. The surgical microscope according to claim 5, wherein the display system comprises an ocular of the microscopy optics, and wherein the microscopy optics are configured to project the image displayed by the display into a beam path of the ocular.

7. The surgical microscope according to claim 1, wherein the microscopy optics comprise at least one sensor configured to measure the imaging scale and to transmit data representing the measured imaging scale to the controller; and
wherein the controller is configured to obtain the imaging scale of the imaging from the data representing the measured imaging scale.

8. The surgical microscope according to claim 1, wherein the controller comprises a user interface configured to receive data representing a magnification of the imaging desired by a user,
wherein the microscopy optics comprise an actuator for changing the imaging scale, wherein the actuator is controlled by the controller, and
wherein the controller is configured to control the actuator in dependence of the data representing the desired magnification.

9. The surgical microscope according to claim 8, wherein the controller is configured to obtain the imaging scale from the data representing the desired magnification.

10. The surgical microscope according to claim 1, wherein the microscopy optics comprise an objective lens having at least two components being displaceable relative to each other for changing a distance from the objective lens to the field of view.

11. The surgical microscope according to claim 1, wherein the microscopy optics comprise a zoom system for changing the imaging scale for a given fixed working distance.

12. The surgical microscope according to claim 1, wherein the selecting, from the members of the group of plural different surgical tools, of the member corresponding to the surgical tool in the camera images uses a technique selected from a group of techniques, wherein the group of techniques comprises a template matching technique, a sliding window technique, and a Hough voting technique.

* * * * *